United States Patent [19]

Tadros

[11] Patent Number: 5,078,007
[45] Date of Patent: Jan. 7, 1992

[54] IN-LINE POLYMER MELT

[75] Inventor: Safwat E. Tadros, Claymont, Del.

[73] Assignee: E. I. Du Pont de Nemours and Company, Wilmington, Del.

[21] Appl. No.: 544,626

[22] Filed: Jun. 27, 1990

[51] Int. Cl.⁵ .................................... G01N 11/04
[52] U.S. Cl. ......................................... 73/56
[58] Field of Search ........................ 73/56, 55, 60

[56] References Cited

U.S. PATENT DOCUMENTS

| | | | |
|---|---|---|---|
| 3,841,147 | 10/1974 | Coll et al. | 73/56 |
| 4,213,747 | 7/1980 | Friedrich | 425/144 |
| 4,241,602 | 12/1980 | Han et al. | 73/56 |
| 4,468,953 | 9/1984 | Gerritamo | 73/60 |
| 4,541,270 | 9/1985 | Hanslik | 73/56 |
| 4,721,589 | 1/1988 | Harris | 264/40.1 |

FOREIGN PATENT DOCUMENTS

2454600 5/1976 Fed. Rep. of Germany .......... 73/56

Primary Examiner—Hezron E. Williams
Assistant Examiner—Joseph W. Roskos
Attorney, Agent, or Firm—Paul R. Steyermark

[57] ABSTRACT

An apparatus and a process for quickly and accurately determining in-line the rheology of molten polymer streams, said apparatus comprising a cam member and a pressure wall member, one of which is a rotating member and the other one is a stationary member, the rotating member dragging molten polymer into a wedge-shaped clearance between the cam member and the pressure wall member, polymer pressure within the clearance being sensed by a pressure detection device capable of producing a signal responsive to said pressure in the form of a display, a graph, or an arbitrary numerical value, but preferably being transmitted to a computer programmed to calculate apparent melt viscosity of the polymer by the application of the Reynold's theory of lubrication.

19 Claims, 8 Drawing Sheets

IN-LINE POLYMER MELT RHEOMETER

BACKGROUND OF THE INVENTION

This invention relates to a novel in-line melt rheometer capable of producing reproducible and accurate measurements of polymer rheology, and especially of apparent polymer viscosity at practical shear rates.

Knowledge of polymer rheology is very important for efficient design and monitoring of polymer melt-processing operations. Polymer melt viscosity affects its rate of flow as well as its ability to fill molds. Since polymer rheology is dependent on several factors, including the molecular weight of the polymer, melt morphology, and physical structure, it is a property suitable for monitoring possible changes of molecular weight, changes in melt elasticity, and changes of morphology of the polymer during melt processing, so that processing conditions can be adjusted accordingly.

While the importance of accurate rheology measurements during melt processing has always been recognized, and some equipment was available for determining polymer melt viscosity, especially in sampling side streams, there has heretofore existed no practical method or fast response equipment for determining in-line melt viscosity of polymers, especially of filled, e.g., fiber-reinforced polymers and of other highly viscous polymer compositions over a broad range of shear rates, especially at high shear rates. Normally, a sample of such a composition had to be removed from the melt processing equipment such as, for example, an extruder and tested in a melt indexer or other suitable apparatus. This normally was a long operation, so that there always was a time lag between polymer sampling and melt viscosity determination. This naturally had the shortcoming of making it impossible to adjust melt processing conditions as soon as a departure from the desired predetermined standard occurred. Equipment used for side stream rheology measurements had slow response of about 10 minutes or more and, therefore, could not provide rapid feedback for accurate process control. Besides, such equipment was not measuring properties of a truly representative process stream.

There has always existed, therefore, a great need for a practical means for quickly and accurately determining the melt rheology of polymers during their melt processing.

SUMMARY OF THE INVENTION

According to the present invention, there is now provided an apparatus and a process for quickly and reproducibly determining the melt rheology of a polymeric material being conveyed or plasticated in melt processing apparatus, said melt rheology-determining apparatus comprising at least one pair of cam means and pressure wall means, adjacent thereto but spaced therefrom by a small distance, one of the members of said pair being a rotating member and the other one being a stationary member, both members being mounted within said melt processing apparatus in such a manner that they are in continuing contact with the molten polymeric material being conveyed or plasticated, said cam means being shaped or mounted in such a way that it is capable of inducing pressure increases and decreases within molten polymeric material flowing through the space between it and the pressure wall means, so that there results at least one pressure maximum and one pressure minimum with every rotation of the rotating member; said rotating member being driven by a driving means imparting to said rotating member its rotary movement;

said pair of cam means and pressure wall means being arranged in such a spatial relationship to each other that a wedge-shaped clearance is defined between the edge of said cam means and said pressure wall means, said wedge-shaped clearance either decreasing or increasing in the direction of rotation of said rotating member and being in operative contact with a sensor means capable of detecting a physical phenomenon which is either the pressure or the shear stress of the molten polymer within said space and generating a signal responsive to said physical phenomenon;

the signal generated by said sensor means being transmitted to a device capable of recording or displaying the values of said phenomenon detected by said sensor means or, optionally, of converting said signal into a meaningful representation of apparent polymer melt shear viscosity value and of returning said value.

BRIEF DESCRIPTION OF THE DRAWINGS

FIG. 1a is a drawing of two inclined surfaces moving relative to each other and shows selected velocity profiles of a viscous fluid dragged into the narrowing space between these surfaces, while

FIGS. 2a through 2c represent one possible embodiment of this invention, where a single-taper cam is mounted on the shaft of a single screw extruder. FIG. 2a is a longitudinal cross-section; while

FIGS. 6a through 6c represent a possible embodiment of this invention, where a stationary taper cam forms part of the inner wall of an extruder barrel.

DETAILED DESCRIPTION OF THE INVENTION

Theory of the Invention

Figure 1A:
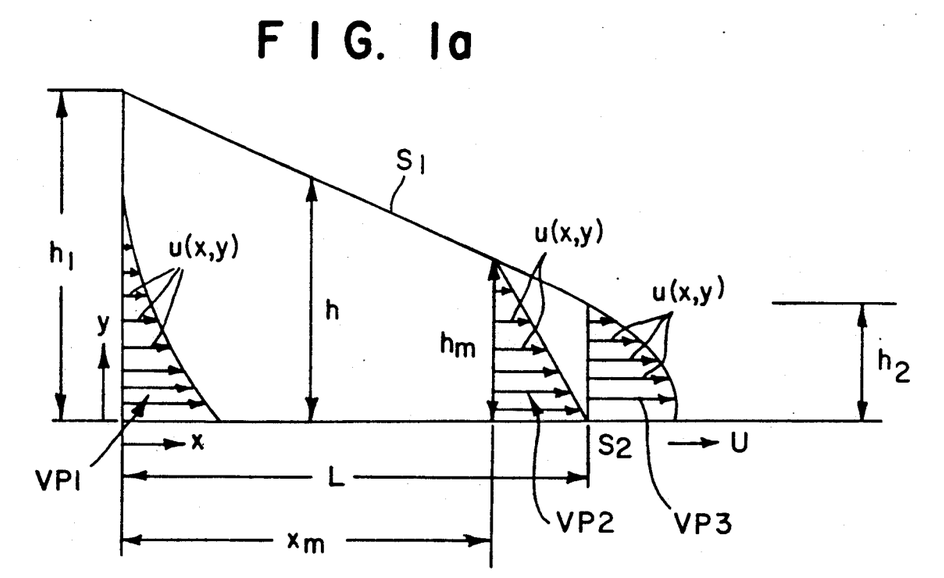

The apparatus of the present invention operates on the principle of the well known Reynold's hydrodynamic theory of lubrication, which has now been extended to this polymer melt application. The details of this theory are discussed in many textbooks of fluid mechanics and lubrication engineering. Referring to FIG. 1a, let us consider two surfaces, S1 and S2, having a relative velocity U, being slightly inclined with respect to each other and separated by a small, decreasing, distance h. These two surfaces define a wedge-shaped space, sometimes hereafter referred to as clearance. For the purpose of this explanation, let us further assume that $S_1$ is fixed, while $S_2$ moves from left to right, as shown by the arrow below the abscissa, and that these surfaces are immersed in a viscous fluid. As surface $S_2$ moves, it will drag with it the fluid, which will become wedged into the clearance; and large pressures will develop within the fluid.

VP1, VP2, and VP3 are representative velocity profiles along the length of the clearance (L), which is plotted on the x axis. VP1 is the profile at the beginning of the clearance (the largest opening); VP3 is the profile at the end of the clearance (the smallest opening); and VP2 is the profile at the location of maximum fluid pressure. The horizontal arrows within those curves indicate the magnitude of fluid velocity in the x direction (u) as a function of the opening of the clearance, which is plotted on the y axis. The meaning of all the reference characters in this drawing is given below.

Figure 1B:
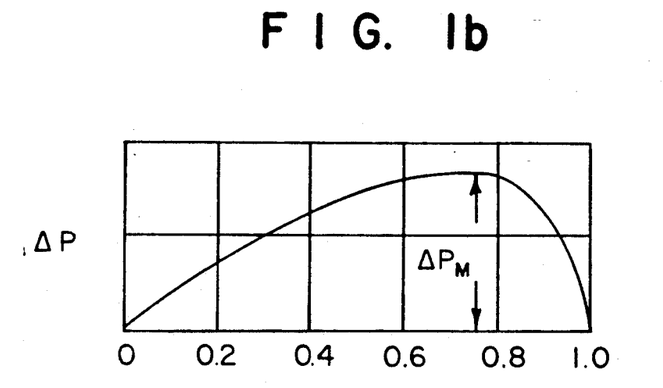
FIG. 1b is a graph representing the distribution of pressures generated by that motion.

FIG. 1b is a plot of pressure change, $\Delta P$, of the fluid wedged into the clearance versus fraction of the length of the clearance. This plot, as well as other plots of pressure of the fluid vs. another variable, especially time, will be sometimes referred to hereafter as pressure profiles.

In order to facilitate the understanding of the following discussion of the theory underlying this invention, as well as of the explanation of the operation of the apparatus of this invention, it is desirable to provide a glossary of various abbreviations used throughout the present disclosure, which are as follows:

h = variable distance between two inclined surfaces, $S_1$ and $S_2$, moving relative to each other;
$h_1$ = maximum distance between surfaces $S_1$ and $S_2$;
$h_2$ = minimum distance between surfaces $S_1$ and $S_2$;
P = pressure developed within a fluid flowing between $S_1$ and $S_2$;
$P_m$ = maximum pressure developed within a fluid flowing between S1 and S2;
$h_m$ = distance between surfaces $S_1$ and $S_2$ where maximum pressure, $P_m$, develops (dP/dx=0);
$P_O$ = pressure of the fluid outside the clearance;
x and y = Cartesian coordinates, x in the direction of movement of surface $S_2$, and y normal to x;
$x_m$ = the position of $P_m$ along the x axis;
u = fluid velocity in the x direction;
L = the length of the clearance;
W = the width of the clearance (not shown in FIG. 1);
N = the speed of rotation, in rpm;
$\eta$ = viscosity, in Pa.sec
$\gamma$ = shear rate, in reciprocal seconds
$Y_{av}$ = average, or apparent, shear rate, in reciprocal seconds;
$\tau$ = local shear stress, in MPa.

For the purpose of the present invention, the following assumptions will be made:

- The distribution of forces is two-dimensional, along the x and y axes;
- Only viscous forces are considered;
- P is independent of y, which means that pressure variations across the clearance are ignored;
- the velocity distribution is the same as if the surfaces were parallel;
- the molten polymer satisfies the conditions of steady laminar flow for Newtonian fluids;
- the fluid is incompressible, has a constant viscosity, and is at constant temperature.

Because molten polymers are known to be non-newtonian fluids, the assumption that molten polymer behaves like a newtonian fluid is incorrect. However, this assumption simplifies the calculations and, further, it does not introduce a significant error into the process of this invention because this departure from the assumed character only affects the calculation constant, which changes with calibration.

Polymer melt in melt-processing apparatus contains no gases or bubbles that would affect pressure and behaves like an incompressible fluid. Under the conditions of the present invention, its viscosity does not change as local temperature changes because the rheometer of this invention determines average values, and temperature changes are very fast.

The fundamental constitutive equations of continuity and motion for flowing fluid are known; see, for example, *Boundary Layer Theory*. H. Schlichting, McGraw-Hill Book Company, Inc., New York, Sixth Edition, 1968, pages 44-64 and 104-114. The solution of these equations can be written as shown below:

$$P(x) = P_0 + 6\eta U \frac{x(L-x)(h_1 - h_2)}{L h^2 (h_1 + h_2)} \quad (1)$$

Equation (1) gives the pressure profile along the x axis, as shown in FIG. 1b.

$$u(x,y) = \frac{1}{2\eta} \frac{dP}{dx} (y^2 - hy) + U\left(1 - \frac{y}{h}\right) \quad (2)$$

Equation (2) gives the velocity profiles as a function of the fluid's location (x and y) in the clearance, as shown in FIG. 1a.

Therefore, $$\gamma(x) = \left. \frac{du}{dy} \right|_{y=h} = \frac{h}{2\eta} \frac{dP}{dx} - \frac{U}{h} \quad (3)$$

$$\frac{dP}{dx} = 6\eta U \frac{h - h_m}{h^3} \quad (4)$$

where $$h = h_1 - \frac{x}{L}(h_1 - h_2), \quad (5)$$

and $$h_m = \frac{2h_1 h_2}{h_1 + h_2} \text{ at } x_m = \frac{h_1 L}{h_1 + h_2}. \quad (6)$$

The maximum ordinate of the pressure distribution lies to the right of the midpoint of the wedge-shaped clearance, and its value can be estimated as:

$$\Delta P_m = P_m - P_0 = \frac{3L(h_1 - h_2)}{2h_1 h_2 (h_1 + h_2)} \eta U \quad (7)$$

For a particular wedge geometry we can write, $$\eta = C \frac{\Delta P_m}{U}. \quad (8)$$

where C is a constant.

At the maximum pressure $dP/dx = 0$;

As shown in FIG. 1a, and as follows from equation (2), the velocity profile at the location of maximum pressure, $x_m$, is linear; and the shear rate, from equation (3), is constant. Therefore, the shear rate, $\gamma$, at this local point is:

$$\gamma = \frac{U}{h_m} \quad (9)$$

or, in the case of a rotating surface and a stationary surface, $$\gamma = \text{constant} \cdot \frac{N}{h_m}. \quad (9a)$$

where N is the rotation speed of the rotating surface; and the local shear stress, , is:

$$\tau = \eta \gamma = C \frac{\Delta P_m}{h_m} \quad (10)$$

For the purpose of the present disclosure, the term "apparent melt viscosity" means a viscosity value that does not take into consideration thinning of the polymer due to shear. Whenever the term "viscosity" is subsequently used throughout this disclosure without a further qualifier, it is intended to mean apparent melt viscosity.

There are considered at present two approaches to the measurement of rheology using the above principle. The first approach is to measure the $\Delta P_m$ from the pressure profiles such as that shown in FIG. 1b and changing U or N to estimate the apparent melt viscosity of a polymer at different shear rates. Unlike the situation in such industrial equipment as capillary or slit viscometers, in which the velocity profile always has a parabolic shape, and the shear rate is not constant, the velocity profile in the apparatus of the present invention at $h_m$ is linear (as can be seen in FIG. 1a, VP2), and the shear rate is constant. This is especially true when $W/h_m > 10$, so that the effect of side leakage of fluid is minimal. This approach is suitable for a full process stream or a side stream and for a laboratory rheometer. In this case, one would use equations (8) and (10), but the result would be multiplied by an additional correction factor, $C_F$, to account for the effect of side leakage on the polymer flow within the wedge-shaped clearance, which is mainly a function of the ratio (W/L) of clearance width W (not shown in FIG. 1a) to length L.

Where N is constant, the second approach is to measure local P values along the clearance from the pressure profile and calculate the average (or apparent) shear rates along the clearance to estimate the polymer melt viscosity at those shear rates; see equations (11) and (12), below. This approach is more suitable for in-line process measurement because U in most cases is constant.

$$\eta = \frac{L(h_1 + h_2) h^2 \Delta P}{6U(h_1 - h_2) \cdot x \cdot (L - x)} \quad (11)$$

$$\gamma_{av} = \frac{U}{h} \quad (12)$$

When surfaces $S_1$ and $S_2$, and thus the resulting clearance between them, are curved, and the variation of h along the x axis is not linear, the general equation for hydrodynamic films may be applied to the converging geometric wedge of the journal bearing. For a particular geometric wedge configuration, one can still write the following equation (13):

$$\eta = \text{const} \cdot \frac{\Delta P}{N} \quad (13)$$

While the above theory offers a very simple way to study polymer melt properties, it may have to be modified to account for non-Newtonian behavior as well as for the viscous heat generation effect on temperature-dependent viscosity.

Finally, it is assumed that equations developed for rectangular coordinates are applicable to data obtained in cylindrical coordinates, especially as the size of the equipment increases.

Apparatus

The apparatus of the present invention can be installed in any type of equipment in which polymers are conveyed, mixed, extruded, molded, or otherwise processed in the melt. Such equipment includes, among others, extruders, blenders, gear pumps, and injection molding equipment, especially, gates and mold sprues.

The most obvious type of melt-processing equipment in which an apparatus of the present invention can be installed is an extruder, which may be of a single screw or twin-screw type and of a variety of screw designs. The cam means most conveniently is the rotating member and is installed on the screw shaft, so that it rotates in the same direction and at the same speed as the screw. A wedge-shaped clearance is defined between the cam and the extruder barrel, which serves as the stationary pressure wall means. It is possible, however, to reverse the design, so that a stationary cam is mounted on the inner wall of the extruder barrel, while a cylindrical rotary member is mounted on the screw shaft. Because viscosity is proportional to the ratio of change of pressure in the clearance to the speed of rotation, $(\Delta P/N)$, it is necessary for this alternate design to know exactly the speed of rotation of the screw, which is determined by means of a tachometer.

Figure 2A:
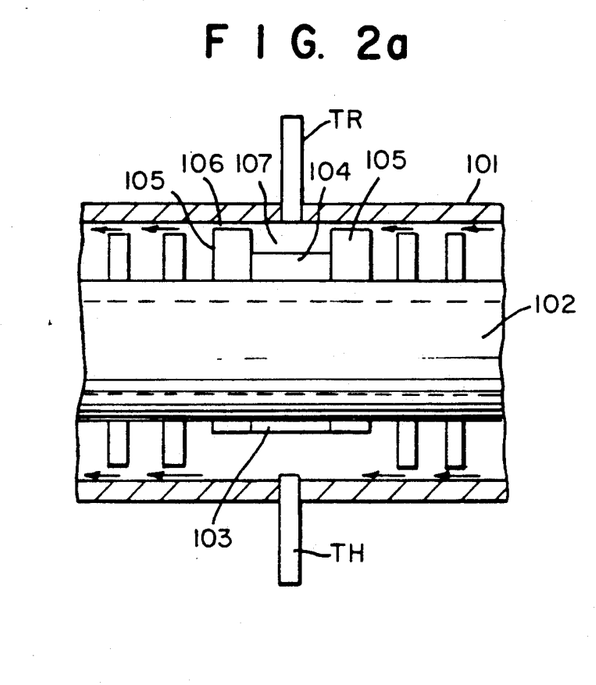
Figure 2B:
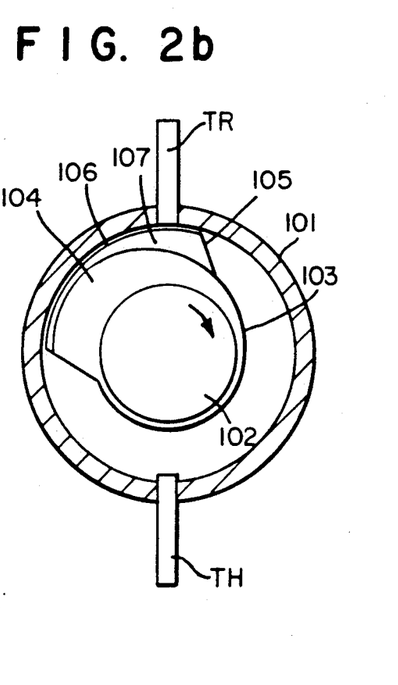
FIG. 2b is a transverse cross-section.
Figure 2C:
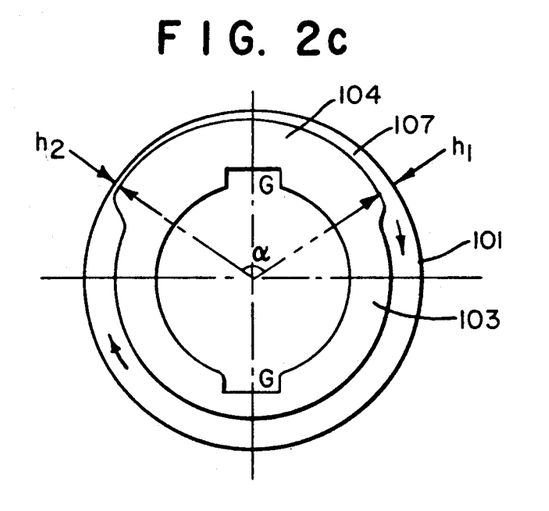
FIG. 2c is a schematic drawing of another single-taper cam within an extruder barrel, other construction details being omitted.

The preferred device is illustrated in FIGS. 2a through 2c, which show two cross-sections of a single screw extruder with a tapered cam according to this invention mounted therein. FIG. 2a is a portion of the longitudinal cross-section, while FIG. 2b is a transverse cross-section. In these drawings, 101 is the extruder barrel; 102 is the extruder screw; 103 is the body of the cam, which has a tapered portion, or taper, 104; 105 are optional cam guards, which are designed to minimize side leakage of molten polymer and thus maximize molten polymer pressure caused by the polymer flow towards the smaller end of the wedge-shaped clearance; TH is a melt thermocouple; and TR is a fast response pressure sensor, most conveniently, a pressure transducer. In FIG. 2a, cam 103 is installed on the extruder screw 102 at a location intermediate the end and the beginning of the extruder screw 102. The cam guards 105 are shaped as segments of a circle having the same radial angle as the taper 104 and a radius intermediate the distance from the center to the highest point of the taper and the inside radius of the extruder barrel, as shown in FIG. 2b. The cam guards thus leave a small peripheral clearance 106 between their edge and the extruder barrel. While the guards 105 shown here rotate with the cam, they do not have to; they can be fixedly attached to the extruder barrel 101. Stationary cam guards suffer less wear than rotary guards and are especially suitable in such applications as gear pumps. The arrows in FIG. 2a show the direction of polymer flow along the barrel. In FIG. 2b, an arrow shows the direction of cam rotation. Molten polymer flowing along the barrel 101 comes in contact with the rotating cam 103, which drags the polymer into the wedge-shaped clearance 107 between the taper 104 and the barrel 101. When the taper 104 of cam 103 is aligned with the pressure transducer TR, as shown in FIG. 2b, the transducer senses the local pressure of molten polymer at the wall created by the flow of the polymer produced by the cam 103 towards the smaller end of clearance 107. The transducer then generates a signal, which is transmitted to a suitable display, recording, or conversion device. This may be, for example, a voltmeter, an oscilloscope, a chart plotter, or, preferably, a programmed computer; and the output may be a plot representative of the pressure profile, or else a number corresponding to the calculated value of apparent melt viscosity at the measured melt temperature and operating shear rates.

FIG. 2c shows schematically a single taper cam mounted within an extruder barrel. Cam 103 is mounteed concentrically with barrel wall 101. Taper 104 has a low side, spaced from the extruder barrel wall by a distance $h_1$, and a high side, spaced from the extruder barrel wall by a distance $h_2$. The taper defines a clearance 107 between its outer edge and the barrel wall. This drawing also shows the radial angle, $\alpha$, of taper 104. G are mounting grooves. The arrows show the direction of rotation of the cam, although the cam could rotate in the opposite direction and would produce a similar effect on the polymer. When the rotation is in the opposite direction, the fluid pressure generated by the cam, $\Delta P$, will be subtracted from the average process pressure, instead of being added to it. This would be advantageous in certain high pressure applications as well as in the case of highly contaminated process streams, to protect the pressure transducers and improve their service life.

In the simplest case, the apparatus of the present invention will be used for in-line quality monitoring and control of polymer rheology. For this purpose, it will be sufficient to establish a typical instrument output characteristic of a polymer having satisfactory rheology, for example, an oscillogram or a chart plot, and to adjust the polymer production parameters so that a polymer producing comparable instrument output under the same measurement conditions is obtained. Once the melt viscosity of the polymer has been determined, whether in the apparatus of this invention or in a conventional laboratory apparatus, it is not necessary to convert the signal produced by the sensor means to actual melt viscosity or other rheology value, so long as the predetermined value, scan, or plot is consistently obtained.

However, in many other situations it is desirable to be able to predict or calculate the exact melt viscosity or other rheological property of a polymer; and for this purpose it is appropriate to direct the signal produced by the sensor means to a programmed computer capable of converting the signal into the actual numerical value.

Figure 3:
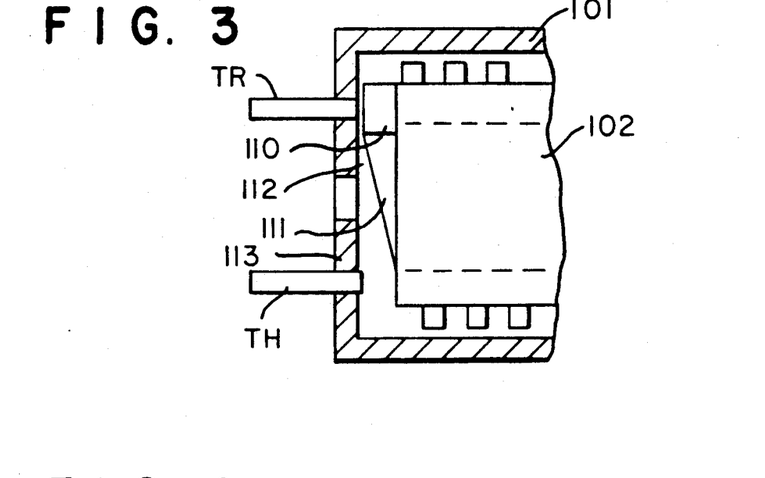
FIG. 3 represents a longitudinal cross-section of another embodiment of this invention, where a cam of a different design is placed at the end of the shaft of a single screw extruder.

FIG. 3 illustrates in a longitudinal cross-section the embodiment in which a cam 110 of a different design is mounted at the end of extruder screw 102. As in FIG. 2, 101 is a portion of the extruder barrel; TH is a melt thermocouple; and TR is a pressure transducer. Cam 110 in this embodiment, instead of a tapered portion extending in a radial direction from its body, has a tapered portion 111 formed in the axial direction. In this design, a wedge-shaped clearance 112 is formed between the tapered portion 111 and the end wall of the extruder barrel 113.

Figure 4:
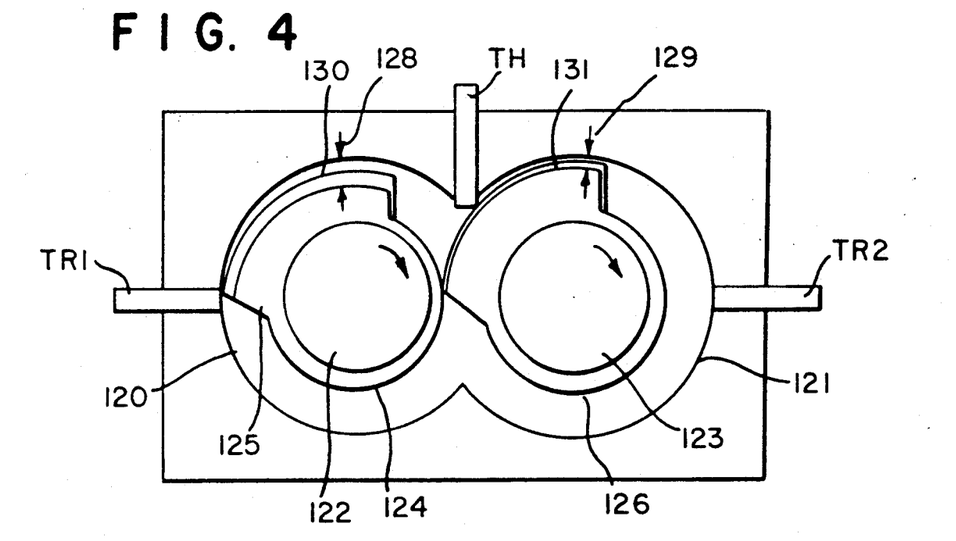
FIG. 4 represents a transverse cross-section of a preferred embodiment of this invention, where two single-taper cams are mounted on the shafts of two corotating screws of a twin-screw extruder.

FIG. 4 is a transverse cross-section of a twin-screw extruder. It shows two cams 124 and 126 mounted within barrels 120 and 121 on the shafts of two corotating screws 122 and 123. The cams have tapered portions 125 and 127 and rotate in the direction shown by arrows. Pressure transducers TR1 and TR2 sense the molten polymer pressures in wedge-shaped clearances 128 and 129, when the tapers of the cams are aligned with the transducers, as shown in FIG. 4. Cam guards 130 and 131 are shown behind tapers 125 and 127. The varying radii of taper 127 are larger than the corresponding varying radii of taper 125, so that cam 126 in most cases will generate a higher pressure amplitude than cam 124 because of a higher shear rate. It is to be noted that, at very high shear rates, polymer may degrade to a lower molecular weight material, and its melt pressure can be quite low. This also may be the case for polymer melts that undergo a large reduction of viscosity, due to shear thinning, at high shear. In this case, the maximum pressure generated by cam 126 may be lower than that generated by cam 124. This, however, will not affect the suitability of this apparatus for viscosity determination since a pressure differential, $\Delta P$, will still exist for the calculation purposes for each cam. Temperature of the melt in the barrel is measured by a thermally insulated melt thermocouple TH placed at the intersection of barrels 120 and 121.

In this arrangement, one cam is placed on the shaft of each corotating screw at equal distance from the corresponding ends of both screws, such that surfaces of the cams are self-wiping. In this way, fresh polymer melt is continually sampled by the transducers TR1 and TR2 in clearances 128 and 129. Transducers TR1 and TR2 are installed on opposite sides of the barrels, preferably so that the transducer diaphragms are flush with the extruder walls. They can be recessed up to about 2 mm within the the extruder walls to protect them from damage. The tip of thermocouple TH must protrude beyond the extruder wall far enough into the melt to be constantly surrounded by flowing molten polymer, but so that it will not hit either cam, as shown in FIG. 4.

Figure 5:
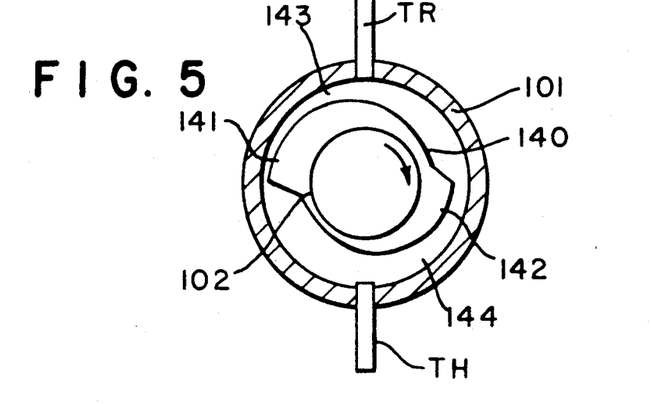
FIG. 5 is a schematic drawing of a two-taper cam mounted inside an extruder barrel.

Cam 140, shown in a cross-section in FIG. 5 and mounted on extruder screw 102, has two tapers, 141 and 142, spaced 180° apart. Taper 141 has a larger average radius of curvature and in most cases creates a larger pressure of molten polymer flowing through clearance 143 formed between it and the extruder barrel wall 101 than taper 142, which has a smaller average radius of curvature and creates a lower pressure in clearance 144. Such a cam serves the function of two separate cams, each having a taper of a different size. A cam can have more than two tapers, if desired, and can be used in various applications such as, those where the speed of rotation is slow (e.g., melt gear pumps) or when it is desired to measure multiple shear rates. In this drawing, TH and TR are, respectively, a melt thermocouple and a pressure transducer.

All the embodiments of FIGS. 2, 4, and 5 can be installed in more than one location along the extruder screw to monitor intermediate process steps and can be designed for different specific process shear rates, as the need occurs. Preferred locations in the extruder are between the vacuum port (if any) and the die as well as at the end of the screw.

Figure 6A:
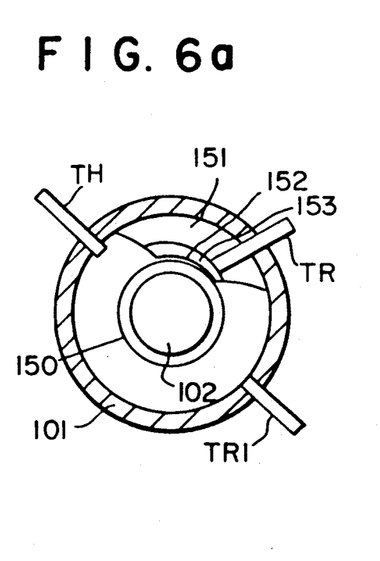
FIG. 6a is a transverse cross-section of a single cam arrangement.
Figure 6B:
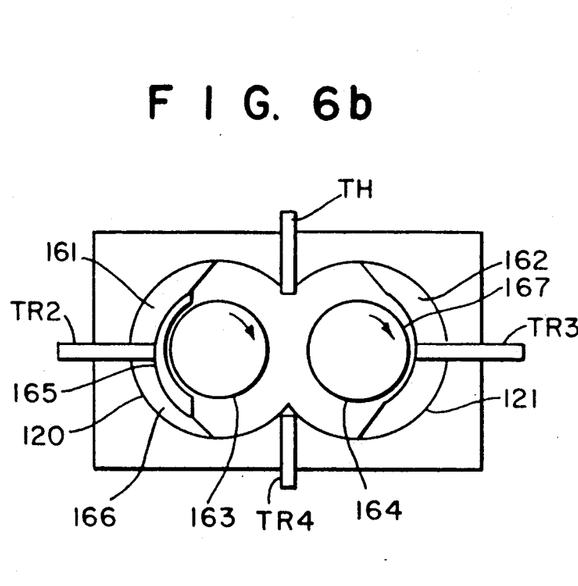
FIG. 6b is a transverse cross-section of a twin-cam arrangement in a twin-screw extruder.
Figure 6C:
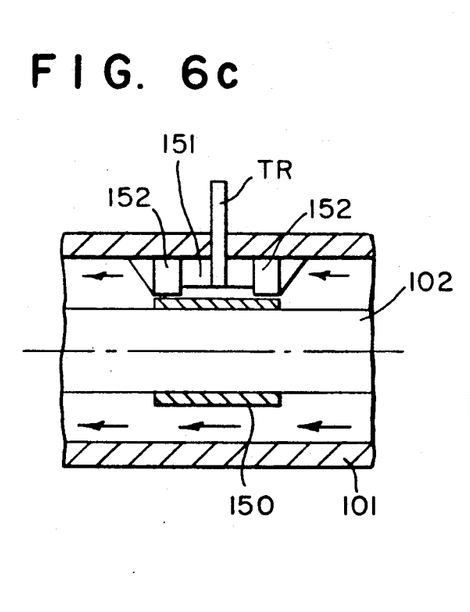
FIG. 6c is a longitudinal cross-section through a single barrel.

FIGS. 6a through 6c represent two alternative embodiments of the present invention, where stationary cam means are mounted on or are part of the inner wall of an extruder barrel. FIG. 6a is a transverse cross-section of a single cam arrangement in a single screw extruder. In this drawing, 101 is the extruder barrel; 150 is a cylinder, which serves as the pressure wall means, concentrically mounted on extruder screw 102; 151 is the stationary cam means, while 152 is a portion of one of two optional guards placed on either side of cam 151. The rotating cylinder 150 drags the polymer melt flowing along barrel 101 into the wedge-shaped clearance 153 between cylinder 150 and cam 151. As before, TR is a pressure transducer, and TH is a melt thermocouple. TR1 is an additional pressure transducer, which measures the process operating pressure, $P_0$, outside cam 151.

It is preferred to locate the presssure transducer TR at distance $x_m$ from the large end of the clearance determined according to equation (6), above. In this way, the highest sensitivity of the pressure transducer TR to viscosity changes in the polymer melt stream will be obtained. One advantage of this embodiment is that in this case the pressure sensed by pressure transducer TR is relatively steady, so that the pressure transducer need not be a fast response instrument and will still provide almost instantaneously accurate readings throughout the process. Further, it will suffer less wear and thus will have a longer service life than it would in other locations.

FIG. 6b shows a variant of this embodiment, where two stationary cam means, 161 and 162, are mounted within barrels 120 and 121 of a twin-screw extruder; 163 and 164 are rotating cylinders mounted on the screws (not shown), which cylinders may be designed to be self-wiping, although not so presented in this drawing; 165 is one of two optional guards placed on either side of cam 161; the corresponding guard for cam 162 is not shown; TR2, TR3, and TR4 are pressure transducers, and TH is a melt thermocouple. The screws are corotating, the direction of rotation being shown by arrows. In this drawing, cam 162 is shown as having smaller inner radii of curvature than those of cam 161, so that it will form a smaller clearance 167 between its inner surface and cylinder 164 than the clearance 166 formed between cam 161 and cylinder 163. Cam 162 will produce a higher shear than cam 161. The rotating cylinders 150, 163, and 164 of FIGS. 6c and 6b, and their associated cams are preferably mounted at the end of the screw, near the die.

FIG. 6c is a longitudinal cross-section through barrel 101 showing cam 151, which is part of the inside wall of barrel 101. While this is a typical representation of either a single screw extruder or a twin-screw extruder, it is assumed for simplicity that this drawing represents the single screw extruder. All the reference numerals correspond, therefore, to those of FIG. 6a.

It is preferred that the direction of movement of the rotary member in contact with the process fluid stream be perpendicular to that stream. This allows good representative sampling and minimizes pressure changes in the direction of the process stream. Although $P_0$ is presumed to be constant, it may not be so in fact. When pressure changes do occur, especially in the crosswise direction, the average value of $P_0$ is used in the calculations.

The rotating member of the melt rheometer of the present invention does not have to be mounted on a functional rotating part of the apparatus in which it is installed, such as the shaft of an extruder screw. The rheometer can be installed, for example, in an autoclave, a reactor, a mixing device, a gear pump, melt spinning gear pump, etc., and the rotating member can be driven by an external motor or other driving means. Therefore, the rheometer can be installed in-line in the full process stream or in a side stream and can be driven by its own driving means at any shear rate or rates needed for process monitoring and control of product quality. Many processes can benefit by employing a rheometer of the present invention, including, for example, reactive compounding, polymerization, melt spinning, extrusion, etc. In melt spinning, melt rheology at the spinneret is critical to the quality control of spun fiber; therefore, one of the preferred applications would be a rheometer mounted in the gear pump or in the spinneret.

In general, the apparatus of the present invention preferably is designed to be operated at about the same shear rate as that of the particular melt-processing operation where the apparatus is being used. This is done by determining the value of $h_m$ for the process speed of rotation N. If desired, the apparatus may be operated instead at the shear rate established in the quality control laboratory, e.g., 1000 sec$^{-1}$. Because of the instantaneous response of the melt rheometer of the present invention, this apparatus is suitable for feedback process control. For example, when N is 300 rpm, the response time is about 0.2 second, which is much faster than previously available side stream devices.

The pressure sensor, especially a pressure transducer, which is an important element of the preferred embodiment of the apparatus of this invention, produces an electrical signal in the form of an analog output, normally within the range of 0-10 volt. The preferred pressure transducers originally were those offered by Dynisco, Norwood, Mass., but equivalent pressure transducers are now offered, among others, by Gentron, Sunnyvale, Calif.; ISI, Winchester, Mass.; and Kulite, Leonia, N.J. In the most preferred embodiment of this invention, this output is digitized and sent to a programmed computer, which calculates polymer melt viscosity versus shear rate by applying the Reynold's equation, as explained above. In addition to the pressure transducer, the apparatus usually also includes a melt thermocouple in contact with polymer melt. Because of the paddling effect of the cam, this makes it possible to also accurately determine the average bulk melt temperature.

It is to be understood that one can equally well make melt rheology determinations based on shear stress measurements according to equation (10), above. For this purpose, one would use a local shear stress sensor instead of the local pressure sensor.

Polymer melt viscosity, which is predicted according to equation (14), below, agrees well with laboratory measurements made with a capillary viscometer according to ASTM D3835-79.

$$\eta_{ST} = C_F \eta \left( \frac{\gamma_L}{\gamma} \right)^{n-1} e^{A\gamma L(T_m - T_L)}, \quad (14)$$

where $\eta_{ST}$ is predicted viscosity corrected for shear rate and temperature; $C_F$ is the calibration constant; $A\gamma_L$ is the Arrhenius constant at laboratory shear rate; n is the power law factor (or power law index), that accounts for shear-thinning behavior of non-Newtonian fluids; $T_m$ is the measured melt temperature in the apparatus; $T_L$ is the laboratory sample melt temperature at which reference viscosity measurement is made; $\gamma$ is the shear rate; and $\gamma_L$ is the laboratory sample shear rate at which reference viscosity measurement is made. It is to be noted that laboratory viscosity determinations must be run in multiple replicates in order to reduce the experimental error.

A laboratory size apparatus of the present invention can be used to determine very accurately the Arrhenius constant, A, for different shear rates by making controlled temperature changes at such different shear rates by changing the rpms while employing external heating or cooling means. Since one has in this instance a continuous polymer melt stream, which is tested at a constant shear rate (N is constant) but at two different controlled temperatures, errors normally introduced by inconsistent sample preparation for a laboratory capillary viscometer are eliminated. It is known that changes in viscosity caused by laboratory errors are of the same order of magnitude as changes in viscosity caused by temperature changes.

One of the preferred designs of the apparatus of this invention is that represented in FIG. 4, that is, two corotating, self-wiping single-taper cams. Both this and a two-taper single cam apparatus (FIG. 5) have a unique capability of reporting the polymer viscosity at a specific shear rate, no matter what the actual shear rates are. This is possible because each taper can be designed for particular clearance dimensions $h_{m1}$ and $h_{m2}$ to provide corresponding shear rates that are within or close to the desired particular shear rate, $\gamma_L$. This feature is advantageous because it permits prediction of apparent polymer viscosity at shear rates other than those measured directly, especially for polymers exhibiting non-Newtonian behavior. Having determined apparent polymer viscosity at more than one shear rate, one can estimate the power law index correlating apparent polymer viscosity to shear rate. For many polymers, the power law index can be used to accurately predict viscosity within a practical process range of shear rates. Further, the Arrhenius constant can be determined by measuring viscosity at different temperatures and then used to predict viscosity at other temperatures.

Another possible embodiment could have two single-taper cams spaced axially on the same screw in a single-screw extruder. This arrangement would have an advantage over a single cam with two tapers because this two-cam arrangement would cause less blockage of polymer flow than a two-taper cam. However, even a single cam with a single taper offers exceptional advantages because of its potentially longer taper than a two-taper cam, so that it can produce higher pressure, and has high sensitivity.

The apparatus and process of this invention are especially well suited for measurements of rheological properties of high viscosity materials. Low viscosity materials would require extremely small clearances and very high sensitivity detection equipment. One of the exceptional advantages of the apparatus and process of this invention is that they can be successfully used for filled polymers, for example, for fiber-reinforced polymers, where the use of capillary viscometers is impractical, while prior art on-line side stream devices require the addition of melt gear pumps. A useful viscosity range is at least about 1-500 Pa.sec. Besides, the present invention permits determinations to be made in-line, without removing samples for measurements in other equipment, such as melt indexers and the like.

Nevertheless, the process and apparatus of this invention could be adapted to the determination of viscosities of fluids other than molten polymers, e.g., concentrated solutions or emulsions of polymers or other materials.

Yet another advantage of the apparatus of the present invention is that it momentarily drags a sample of molten polymer into a constrained area defined by the clearance between the cam means and the pressure wall means of the equipment, where a number of other measurements can be made under controlled flow conditions, including melt temperature measurements and infrared and ultrasound scans. These measurements are more accurate than those made by simply inserting a probe into the extruder barrel because of complex flow patterns and because some flowing molten polymers have a well known tendency to segregate according to viscosities and compositions along their path. For example, more viscous material normally is found adjacent the walls of the barrel, while less viscous material remains near the center of the extruder barrel. However, the molten polymer concentrated in the clearance is a very thorough blend of polymer fractions having different viscosities, so that its properties are truly representative average properties of the polymer flowing through the barrel. The apparatus of the present invention thus is suitable for in situ sampling of polymer. In-line viscosity determinations according to the present invention also permit one to perform statistical counting of contaminants, for example, by counting the incidence of viscosity spikes in a graph.

Tapered cams can be designed and standardized for any particular type of equipment and expected polymer viscosity range. Referring again to FIG. 4, cams 124 and 126 have tapers 125 and 127 of unequal curvatures. For clockwise rotation, the cam with the taper having larger curvature (high shear cam, 126) preferably is mounted on the right hand side when facing the die or exit. In the particular case where this system was installed, the extruder was a Werner & Pfleiderer (W&P) twin-screw extruder, each barrel having an inside diameter of 53.2 mm.

In general, whether for a single screw extruder or for a twin-screw extruder, it is preferred to design the cams so that the clearance defined between the rotating member and the stationary member satisfies the requirement that $h_1/h_2=$ either 2.2 or 3.765 (see FIG. 2c). When this ratio is 2.2, maximum pressure can be obtained for the minimum practical clearance; when it is 3.765, the amplitude of $\Delta P_m$ is maximized for a given cam shear rate. For the particular self-wiping cam design illustrated in FIG. 4, the length of the clearance (and of the cam taper) for a W&P nominal size 53 mm twin-screw extruder is 5.571 cm; and for a W&P nominal size 120 mm twin-screw extruder, it is 12.629 cm. The radial angle, $a$, of the taper is 120° for both (see FIG. 2c). For such cams, the following additional information is provided for the 53 mm extruder and for the 120 mm extruder. In each case, the cam shear rate at $x_m$ was set to 1000 sec$^{-1}$ and thus was identical with the shear rate used in the laboratory to establish reference viscosities.

| $h_1/h_2$ | 53 mm Extruder | | | | 120 mm Extruder | | | |
|---|---|---|---|---|---|---|---|---|
| | 2.2 | | 3.765 | | 2.2 | | 3.765 | |
| N* | 200 | 300 | 200 | 300 | 200 | 300 | 200 | 300 |
| $h_1$** | 0.087 | 0.129 | 0.129 | 0.190 | 0.197 | 0.292 | 0.292 | 0.431 |
| $h_2$** | 0.040 | 0.059 | 0.034 | 0.050 | 0.090 | 0.133 | 0.077 | 0.115 |
| $h_m$** | 0.054 | 0.081 | 0.056 | 0.084 | 0.123 | 0.183 | 0.122 | 0.181 |

*extruder screw rpm
**in cm

Figure 7:
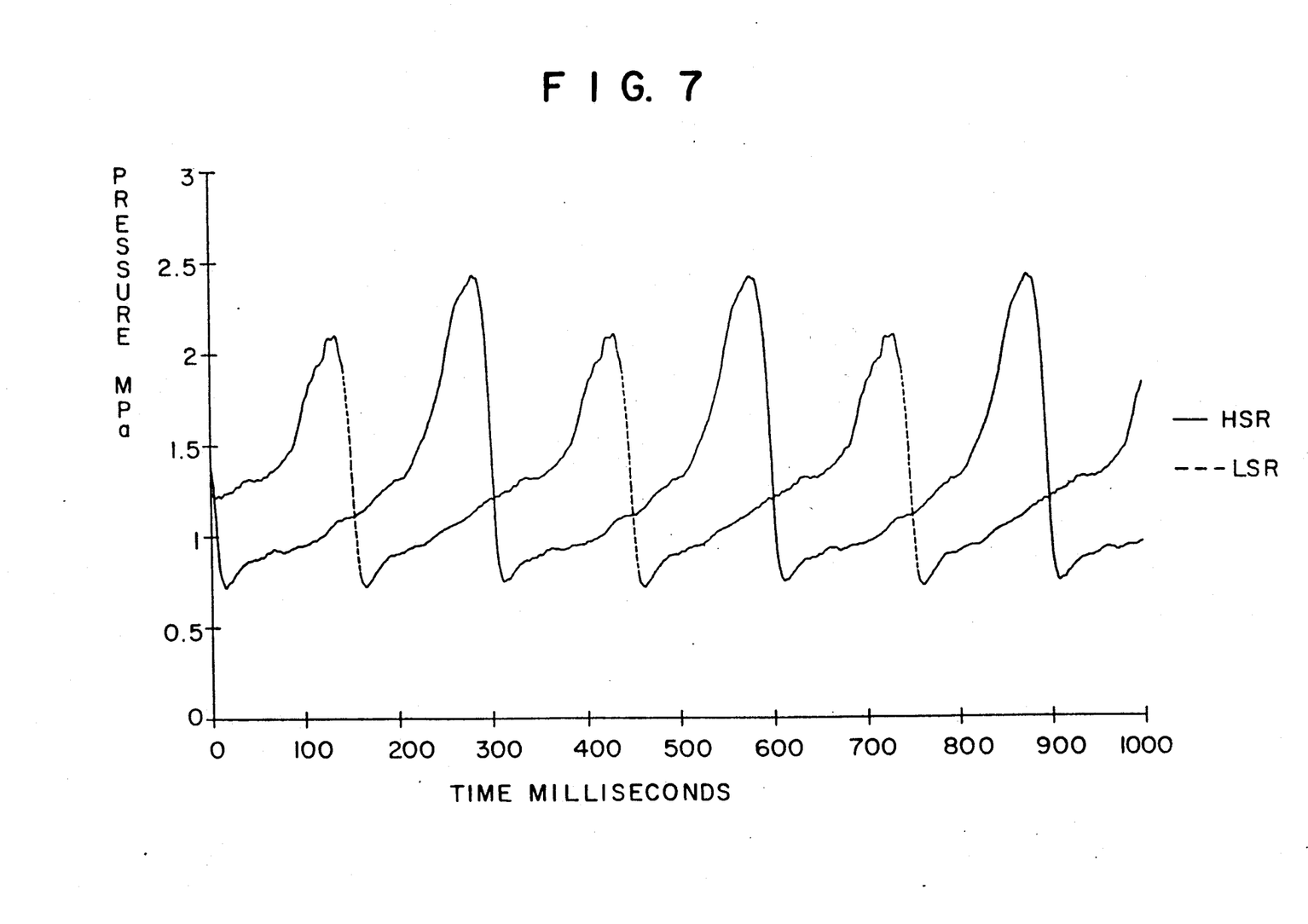
FIG. 7 is a plot of pressure vs. time obtained with an apparatus corresponding to FIG. 4.

FIG. 7 is a typical plot of pressure (MPa) vs. time (millisec.) generated for polyethylene having a melt index of 15 g/10 min, according to ASTM D1238-79, by the high and the low shear rate cams of a melt rheometer of the present invention according to FIG. 4, above, installed in a 53 mm W&P twin-screw extruder. In this case, $h_m$ for the high shear cam was 0.54 mm and for the low shear cam 0.81 mm. The $h_1/h_2$ ratio in both cases was 2.2, and the width of the cam was 20 mm, guards being placed on each side. Since the pressure transducers TR1 and TR2 were installed at 180° from each other, the peaks of the pressure profile for the low shear cam (LSR) were located about midway between the peaks of the pressure profile for the high shear cam (HSR).

Figure 8:
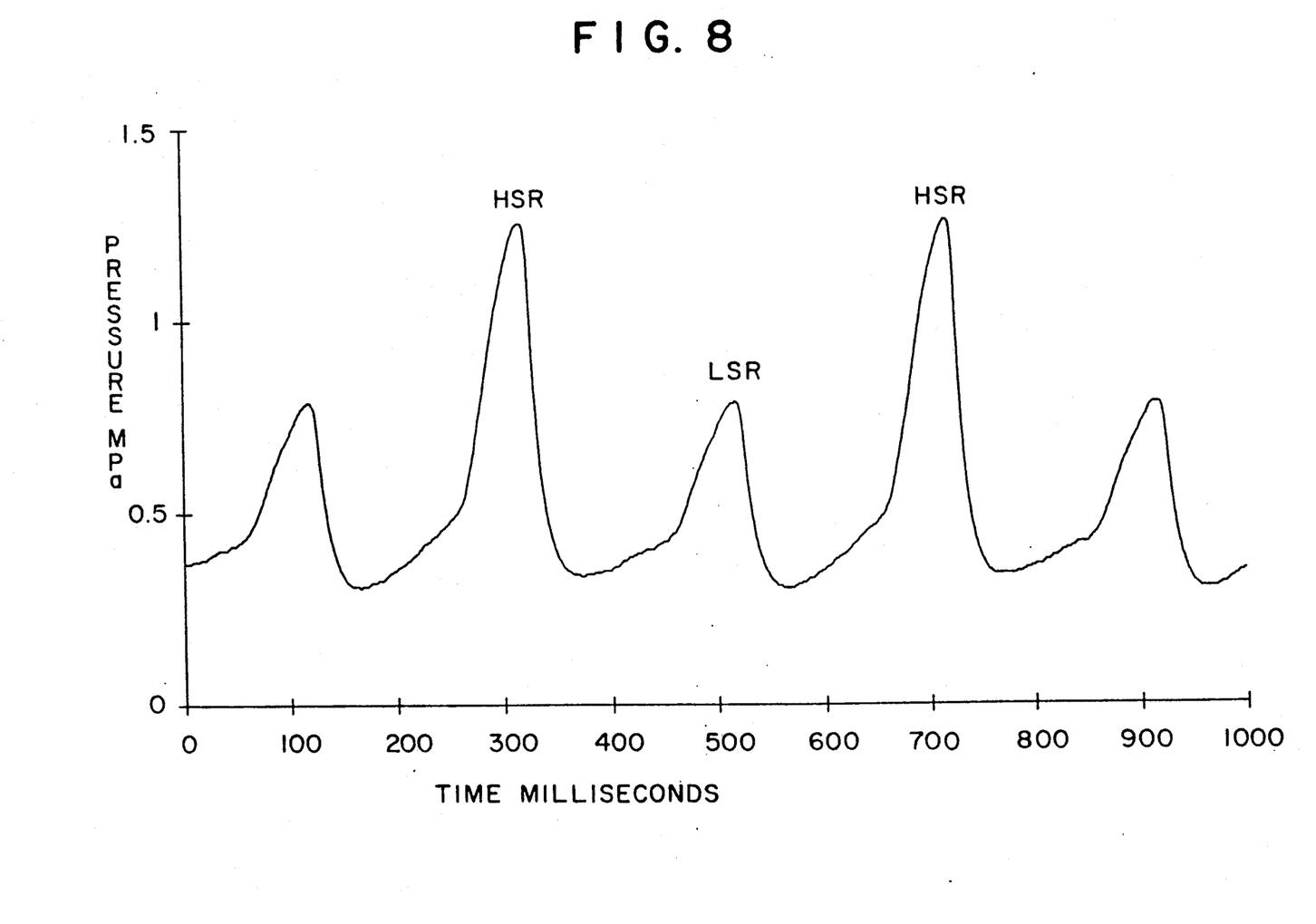
FIG. 8 is a plot of pressure vs. time obtained with an apparatus of FIG. 5.

FIG. 8 is a typical plot of pressure (MPa) vs. time (in milliseconds) generated by a cam having two tapers spaced 180° apart, according to FIG. 5, above. The plot has alternating peaks corresponding to the high shear taper (HSR) and to the low shear taper (LSR).

Pressure profiles such as those represented by the plots of FIGS. 7 and 8 are characteristic of particular polymers and can be used for determining other rheological properties of polymers, in addition to their melt viscosities. Thus, the time shift between pressure peaks is indicative of polymer melt viscoelasticity, especially when cams of two different shear rates are used, the higher the shift the higher the melt viscoelasticity. The standard deviation for the shift is indicative of relaxation times or of the melt uniformity, the smaller the deviation the more uniform the melt, even when both tapers (or cams) are running at the same shear rate. Also, when both tapers are running at the same shear rate, and the clearance dimensions $h_1/h_2$ for one taper are different from those for the other taper, the $\Delta P_m$ values for both tapers in the case of a newtonian fluid will be the same. But for a non-newtonian fluid, those values will not be the same, and the difference between the $\Delta P_m$ values can be a measure of the fluid's elasticity.

Both melt viscosity and elasticity are sensitive indicators of product quality.

The clearance design is important. Its dimensions $h_1$, $h_2$, L, and W should be chosen so as to allow stable and continuous fluid flow in the clearance and to maximize the fluid pressure within the clearance. Also, side leakage of the fluid should be as small as possible. The clearance design will depend on the expected polymer rheology and on the installation geometry of the apparatus of the present invention. Apparatus with a good clearance design gives stable pressure profiles such as those shown in FIGS. 7 and 8. It is preferred that the W/L ratio be larger than 0.05, most preferably, 0.1 to 5; that the W/$h_m$ ratio be larger than 10, most preferably, 20 to 5000; and that the $h_1/h_2$ ratio be larger than 1, most preferably, 1.5 to 20. Further, the design of clearance dimensions as a function of cam taper angle, $a$, (see FIG. 2c) does not have to be linear as it allows stable fluid flow and pressure within the clearance.

Figure 9:
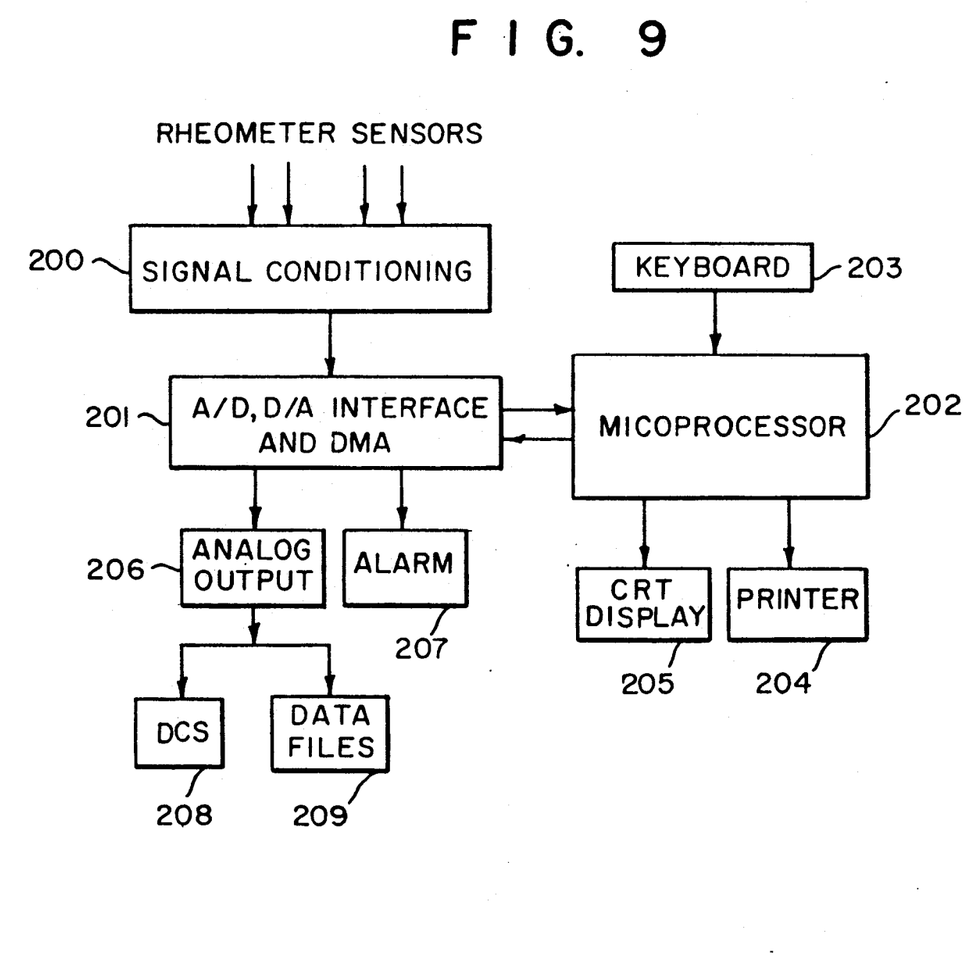
FIG. 9 is a functional block diagram of a preferred embodiment of the process of this invention.

Now, with reference to FIG. 9, this is a typical functional block diagram of a preferred embodiment of this invention, where the signal produced by the sensor means is transmitted to a programmed computer, which processes the signal and returns the desired rheological value.

As is clear from the above discussion, a number of parameters which enter into the mathemathical equations must be known or determined. The apparatus of the present invention must, therefore, be equipped with a variety of sensor means or other measuring equipment. The signals produced by such equipment are conditioned in the signal-conditioning module (Block 200). This module contains equipment such as pressure and temperature amplifiers, pressure difference instrumentation, random noise filters, tachometer-conditioning hardware, power supply, and input-output connecting cables. The conditioned signals are sent to a high speed analog/digital converter interface, A/D, and direct memory access, DMA, (Block 201), which allows direct data transfer to the random access memory of a microprocessor. In this module, the analog signals received from the sensors are converted to digital signals, which can be processed by a programmed microprocessor (Block 202). There, the information received from the sensors is processed to calculate the polymer melt rheology. The results either are printed by means of printer 204, or are displayed on a cathode ray tube (CRT) shown in Block 205, or are both printed and displayed. The keyboard 203 is used to input data to the programmed microprocessor and to define alarm limits. The calculated melt viscosity or other melt property also is continuously reconverted via an analog/digital converter module, A/D, in Block 201 to analog output, which can be presented in the form of a plot. Interface 201 also provides the analog output for Alarm 207. The analog output is proportional to the measured viscosity and can be optionally operatively connected to the distributive control system 208 of the polymer production process to monitor and control product quality or to a data acquisition system 209 to produce documentation files on product quality.

Figure 10:
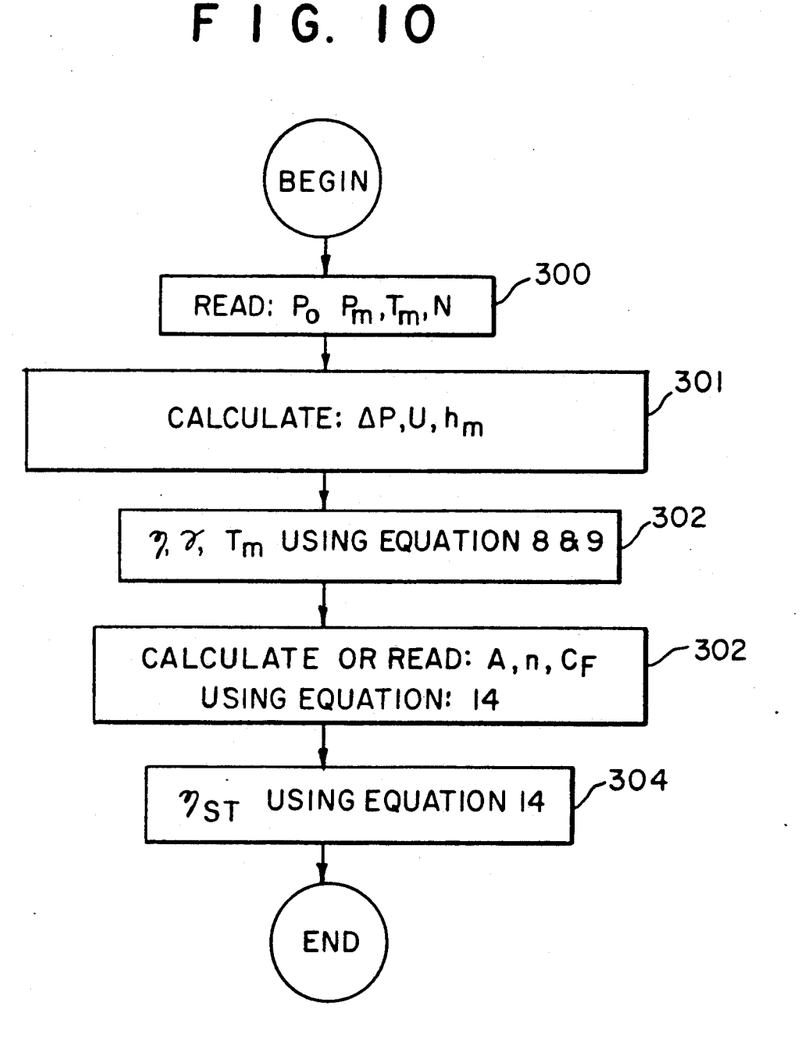
FIG. 10 is a flow diagram of the microprocessor operation of the embodiment of FIG. 9.

FIG. 10 is a typical flow diagram of the operations performed by the programmed microprocessor (Block 202 of FIG. 9) for determining polymer melt viscosity according to this invention. The signals received from rheometer sensors are read in Block 300. These are mainly, $P_O$, $P_m$, $T_m$, and N, which have first been converted to digital form in the analog/digital converter (Block 201 of FIG. 9). In Block 301, the program calculates $\Delta P_m$, the pressure rise produced by the action of the cam means in the clearance, by subtracting the average pressure $P_O$ outside the clearance from the maximum pressure in the clearance $P_m$ (i.e., $\Delta P_m = P_m - P_O$). Alternatively, this also can be done by means of suitable hardware in the signal conditioning unit (Block 200 of FIG. 9). In the case of a rotating tapered cam, the pressure generated by forced flow of polymer melt within the clearance is sensed by a fast response pressure transducer at every turn of the cam, so that $\Delta P_m$ can be simply calculated from the pressure profiles, such as those shown in FIGS. 7 and 8.

Also, in Block 301 the program calculates the speed U, which is equal to 2 §Nr/60, where r is the mean radius of the rotating member, and N is as defined above. Usually, N is provided by a tachometer in the form of a signal, which is read in Block 300. However, in the simplest case, where a rotary cam means is mounted on the shaft of an extruder, N can be calculated from the data of pressure vs. time by calculating the time between peaks or valleys of the pressure profiles.

Further, in Block 301 the program calculates $h_m$ from the clearance dimensions, according to the equation $h_m = 2h_1 h_2/(h_1 + h_2)$.

From all the above information, based on known or measured values, the program calculates the apparent melt viscosity (in Pa.sec) from equation (8), above, and uses equation (9), above, to calculate the measured shear rate.

The output of Block 302 thus is $\beta$, $\gamma$, and $T_m$. These values are then used as input for Block 303, where the predicted apparent viscosity is corrected for shear rate and temperature deviations from laboratory conditions, respectively, $\gamma_L$ and $T_L$. If the values of A, n, and $C_F$ for a particular polymer are stored in the computer data base, this information is read in Block 303. If this information is not available, the program calculates those values from equation (14), above. For example, if N is constant, and the melt temperature between two or more points changes, the program can calculate the Arrhenius constant A. If the melt temperature is constant, but N changes between two or more points, the program can calculate the power law index n. In some large machines, it may be difficult to control temperature as the speed of rotation changes. In that case, one can calculate A and n simultaneously by applying equation (14) at three different points representing meaningful temperature and speed changes. If both A and n are known, the program can calculate $C_F$ by comparing the predicted apparent melt viscosity $\eta_{ST}$ with the laboratory-obtained apparent melt viscosity value $\eta L$, i.e., $C_F = \eta_L/\eta_{ST}$ Therefore, at any instant in the polymer production process, the operation performed in Block 303 calculates $\eta_{ST}$ using equation (14). The output $\eta_{ST}$ is displayed or recorded in Block 304 as the predicted value of apparent viscosity at laboratory conditions. This value also is sent to the digital/analog interface 201 (FIG. 9) to provide an analog output that is proportional to the value of the predicted viscosity. This output can be used to provide in-line control of the process.

The particular computer make and model used in this application was IBM PS/2, Model 30, but other computers having similar capabilities can be used with equal success.

I claim:

1. An apparatus for quickly and reproducibly determining the melt rheology of a polymeric material being conveyed or plasticated in melt processing apparatus, said melt rheology-determining apparatus comprising at least one pair of members, said pair consisting of one cam member and one pressure wall member, adjacent thereto but spaced therefrom by a small distance, one of said members of said pair being a rotating member and the other one being a stationary member, both members being mounted within said melt processing apparatus in such a manner that they are in continuing contact with the molten polymeric material being conveyed or plasticated, said cam member being shaped or mounted in such a way that it is capable of inducing pressure increases and decreases within molten polymeric material flowing through the space between it and the pressure wall member, so that there results at least one pressure maximum and one pressure minimum with every rotation of the rotating member; said rotating member being driven by a driving means imparting to said rotating member its rotary movement;

said cam member and adjacent pressure wall member being arranged in such a spatial relationship to each other that a wedge-shaped clearance is defined between the edge of said cam member and said pressure wall member, said wedge-shaped clearance either decreasing or increasing in the direction of rotation of said rotating member and being in operative contact with a sensor means capable of detecting a physical phenomenon which is either the pressure or the shear stress of the molten polymer within said space and generating a signal responsive to said physical phenomenon;

the signal generated by said sensor means being transmitted to a device capable of recording or displaying the values of said phenomenon detected by said sensor means or of converting said signal, by the application of the Reynold's theory of lubrication, into a meaningful representation of apparent polymer melt viscosity value and of returning said value.

2. The apparatus of claim 1 wherein each cam member has the shape of a taper extending radially from a substantially circular body and is the rotating member.

3. The apparatus of claim 2 which is mounted inside an extruder, each cam member being placed on the shaft of an extruder screw and rotating in the direction of and at the speed of the screw.

4. The apparatus of claim 3, which comprises two cam members mounted inside a twin-screw extruder.

5. The apparatus of claim 4 wherein the screws are corotating, and the cam member sare self-wiping.

6. The apparatus of claim 1 mounted inside a single-screw extruder, the cam member having two tapers of unequal curvatures spaced 180° apart.

7. The apparatus of claim 1 also comprising a thermally insulated thermocouple inserted into the body of the melt-processing apparatus at a location close to the at least one cam member.

8. The apparatus of claim 1 wherein the ratio of the width to the length of the clearance is larger than 0.05.

9. The apparatus of claim 8 wherein the ratio of the width to the length of the clearance is about 0.1 to 5.

10. The apparatus of claim 1 wherein the ratio of the maximum distance between the stationary member and the rotating member to the minimum distance between the stationary member and the rotating member is larger than 1.

11. The apparatus of claim 10 wherein the ratio of the maximum distance between the stationary member and the rotating member to the minimum distance between the stationary member and the rotating member is 1.5 to 20.

12. The apparatus of claim 1 wherein the ratio of the width of the clearance to the distance between the stationary member and the rotating member at the location of maximum pressure within the clearance is larger than 10.

13. The apparatus of claim 1 wherein the ratio of the width of the clearance to the distance between the the stationary member and the rotating member at the location of maximum pressure within the clearance is 20 to 5000.

14. The apparatus of claim 1 wherein the melt rheology-determining apparatus is mounted in a gear pump supplying molten polymer to a spinneret of a melt-spinning apparatus.

15. The apparatus of claim 1 wherein the melt rheology-determining apparatus is mounted within the body of a spinneret of a melt-spinning apparatus.

16. A process for quickly and reproducibly determining the melt rheology of a polymeric material being conveyed or plasticated in melt processing apparatus, said process comprising causing the polymeric material to flow through a melt rheology-determining apparatus of claim 1 mounted inside said melt-processing apparatus and obtaining by means of the recording or display device component of the melt rheology-determining apparatus the value of a physical phenomenon detected by the melt rheology-determining apparatus, which is either pressure or shear stress of the molten polymer, or obtaining by means of said device apparent melt viscosity of the molten polymer derived from the value of said physical phenomenon by the application of Reynold's theory of lubrication.

17. The process of claim 16 practiced with the melt rheology-determining apparatus mounted inside a melt-processing apparatus which is an extruder.

18. The process of claim 16 practiced with the melt rheology-determining apparatus mounted inside a melt-processing apparatus which is a gear pump supplying molten polymer to a spinneret of a melt-spinning apparatus.

19. The process of claim 16 practiced with the melt rheology-determining apparatus mounted inside a melt-processing apparatus which is a spinneret of a melt-spinning apparatus.

* * * * *

UNITED STATES PATENT AND TRADEMARK OFFICE
CERTIFICATE OF CORRECTION

PATENT NO. : 5,078,007

DATED : Jan. 7, 1992

INVENTOR(S) : Safwat E. Tadros

It is certified that error appears in the above-identified patent and that said Letters Patent is hereby corrected as shown below:

On the title page and Col. 1, line 1, delete "IN-LINE POLYMER MELT" and insert -- IN-LINE POLYMER MELT RHEOMETER --.

Claim 5, column 16, line 55, "...cam member sare" should read --...cam members are--.

Signed and Sealed this

Twentieth Day of April, 1993

Attest:

MICHAEL K. KIRK

*Attesting Officer*  *Acting Commissioner of Patents and Trademarks*